United States Patent [19]

Fattori et al.

[11] Patent Number: 5,260,302

[45] Date of Patent: Nov. 9, 1993

[54] ANTIFUNGAL MICROORGANISM

[75] Inventors: Maria Fattori, Valdagno, Italy; Stefaan R. M. Horemans, Korbeek Dyle; Marc Lefebvre, Evers, both of Belgium; Keith A. Powell; Annabel Renwick, both of Berkshire, England

[73] Assignee: Imperial Chemical Industries PLC, London, United Kingdom

[21] Appl. No.: 597,665

[22] Filed: Oct. 17, 1990

[30] Foreign Application Priority Data

Oct. 17, 1989 [GB] United Kingdom ............... 8923407

[51] Int. Cl.$^5$ ................... C12Q 1/04; C12N 1/20
[52] U.S. Cl. .................. 435/34; 435/42; 435/243; 435/253.3; 435/874; 435/876; 435/911; 435/929; 435/939; 424/93 R; 424/93 N; 424/93 Q; 47/57.6
[58] Field of Search ........... 435/34, 42, 243, 253.3, 435/874, 876, 911, 929, 939; 424/93 R, 93 N, 93 Q; 47/57.6

[56] References Cited

U.S. PATENT DOCUMENTS

| | | | |
|---|---|---|---|
| 4,588,584 | 5/1986 | Lumsden et al. | 424/93 |
| 4,647,533 | 3/1987 | Weller et al. | 435/29 |
| 4,798,723 | 1/1989 | Dart et al. | 424/93 |

FOREIGN PATENT DOCUMENTS 0106504  3/1986  European Pat. Off. .
0376775  7/1990  European Pat. Off. .

OTHER PUBLICATIONS

STN No. 90:2313 (Osburn et al).
STN No. 89:294085 (Kaiser et al).
STN No. 90:453178 (Trapero-Casas et al).

Primary Examiner—Michael G. Wityshyn
Assistant Examiner—Abdel A. Mohamed
Attorney, Agent, or Firm—Cushman, Darby & Cushman

[57] ABSTRACT

A method for the screening of potential antifungal agents comprises testing the inhibitory effect of the potential antifungal agent in two tests, a first test for inhibition of pathogen development in sterilised soil infested with mycelium of Pythium spp and a second test against for inhibition of disease development in a growing plant of a species susceptible to disease from damping-off disease complex in the presence of the said complex, identifying agents giving potential inhibitory effect in both tests compared with control and submitting same for further examination. Using this method four particularly useful microorganisms which display antifungal activity in a wide spectrum, shown in further testing and in field trials, of disease fungi have been provided. Methods of using such microorganisms and compositions and compositions containing same are also described.

12 Claims, 2 Drawing Sheets

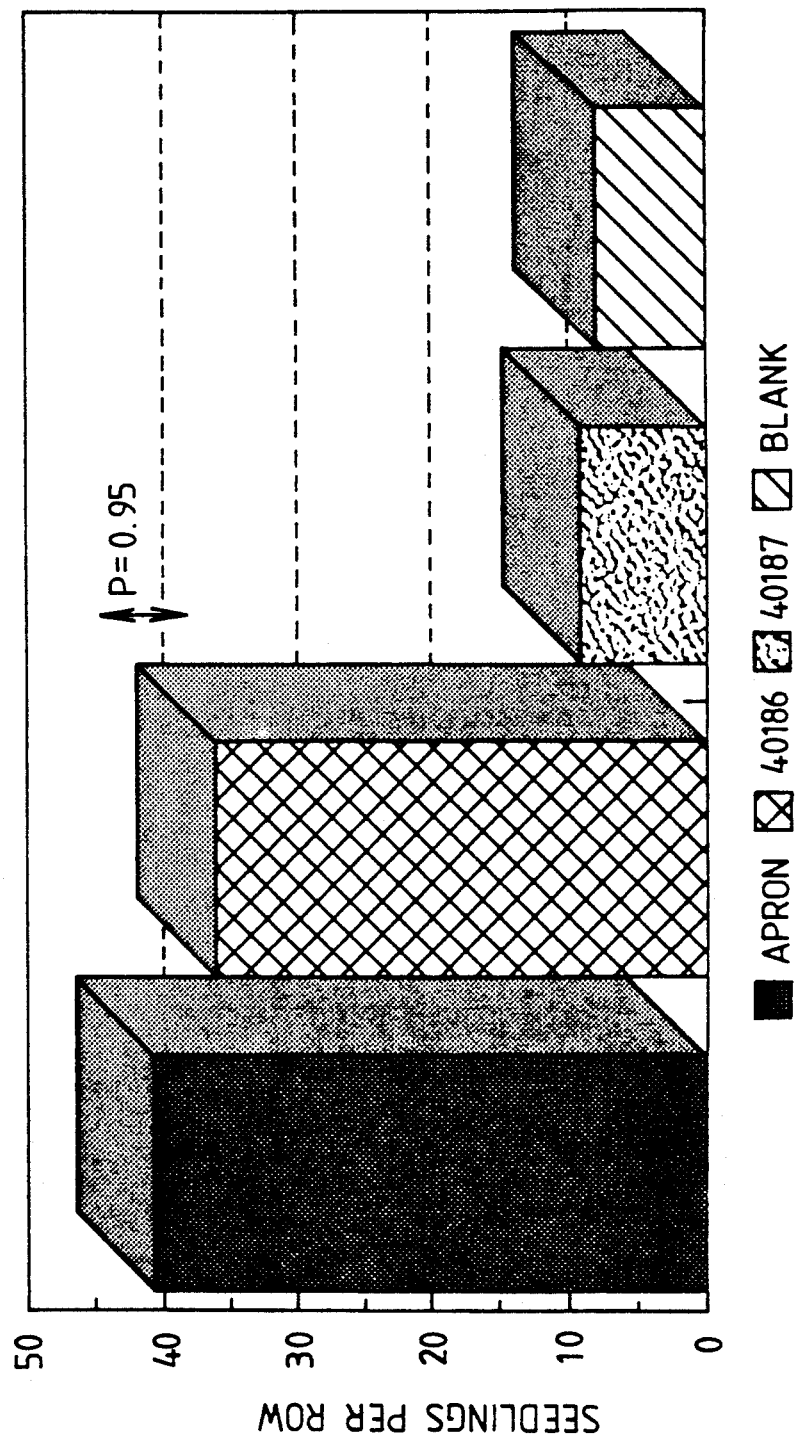
FIG. 1 PYTHIUM TRIALS

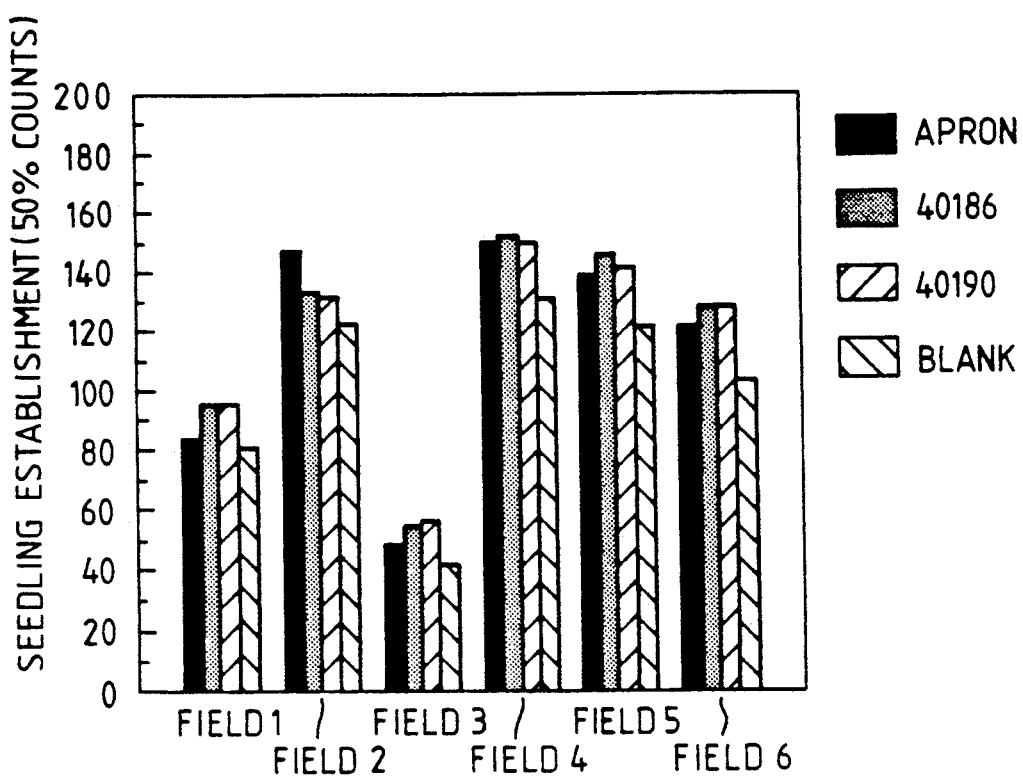
FIG. 2 FIELD TRIALS
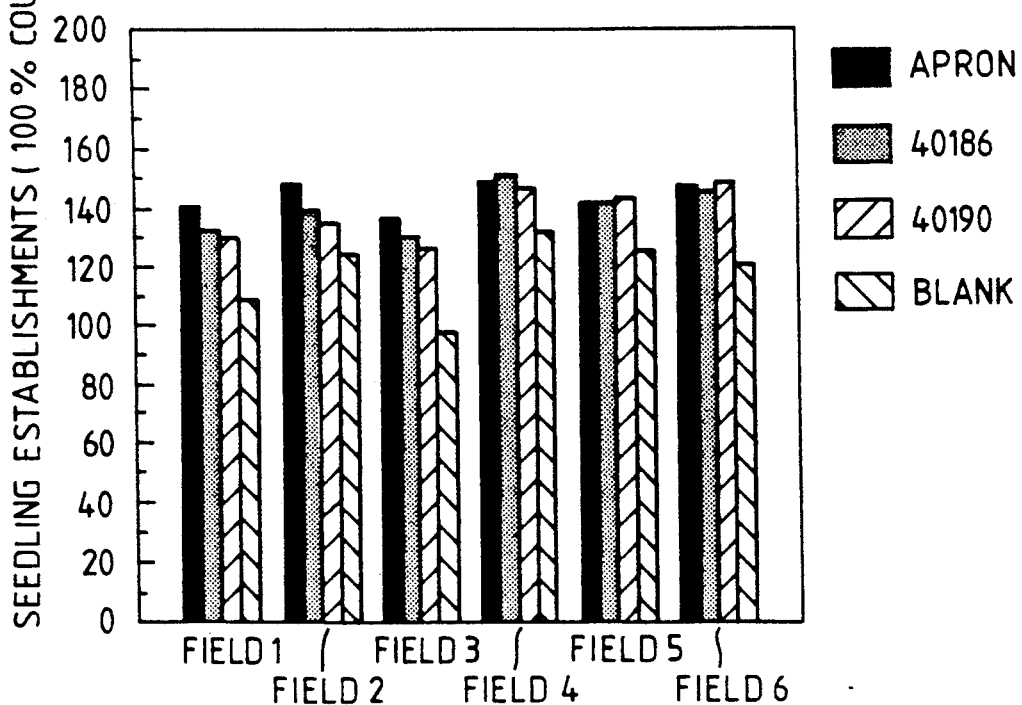
FIG. 3 FIELD TRIALS

ANTIFUNGAL MICROORGANISM

This invention relates to an antifungal microorganism, in particular to novel strains of *Pseudomonas fluorescens*, and the uses thereof for the protection of plants against fungal attack.

It is common microbiological practice to seek microorganisms having interesting properties by screening large numbers, typically many thousands, of isolates from soil for the activity of interest for the intended use. One such use is the isolation of biological control agents (BCAs) which are active against selected plant pathogens. Such BCAs offer alternatives or supplements to chemical agents for pathogen control.

In normal practice, soil samples are taken from field locations where the pathogen of interest appears to be suppressed as this may indicate that microorganisms in the soil itself may be inhibiting the pathogenicity. Microorganisms are then isolated from the individual samples in the laboratory by washing from roots and growth on agar at one or two temperatures which are typical of the optimum temperature for microbial growth, usually from 25° to 30° C. The isolates are then screened initially against a variety of pathogens in agar in a series of petri dishes using the dual culture method. This represents the primary screen. Promising isolates from that screen are then examined more closely in a series of secondary screens which use soil.

In our experience, the traditional primary screen is neither properly nor sufficiently selective of isolates which will ultimately pass through subsequent screening tests and field trials. The traditional primary screen passes large numbers of isolates (typically in the region of 20%) which indicate promise but most of these are rejected in subsequent tests. In addition, we now know that the primary screen, in addition to passing isolates which are subsequently shown to be lack useful activity, fails certain isolates which we now know are quite capable of passing the subsequent screening tests. The outcome of this is that traditional tests pass isolates which are poor and fail isolates which are good inhibitors of pathogenicity.

There is, clearly, a need for a new method of screening soil isolates such as to recover a high number of potentially good isolates and to reject as many of possible of the poor activity materials.

According to the present invention there is provided a method for the screening of potential antifungal agents comprising testing the inhibitory effect of the potential antifungal agent in two tests, a first test for inhibition of pathogen development in sterilised soil infested with mycelium of Pythium spp and a second test again for inhibition of disease development in a growing plant of a species susceptible to disease from a damping-off disease complex in the presence of the said complex, identifying agents giving potential inhibitory effect in both tests compared with control and submitting same for further examination.

The invention is particularly, but not exclusively, useful for the screening of microorganisms from soil samples for potential BCAs but there is no inherent reason why the same procedure of the invention should not be used for chemical agents without any adaptation.

As indicated above, the traditional manner in which the microorganisms may be isolated is not in itself selective: the present invention, therefore also provides a pre-screening method of isolating microorganisms from soil samples which method comprises placing within a sealable container a layer of moist sterile sand, placing the soil sample in moist condition thereupon and sowing in the soil sample a seed of a plant susceptible to the disease of interest, sealing the container, placing the container under environmental conditions conducive to disease development, allowing the seed to germinate and the roots thereof to extend from the soil layer into the sand layer, dissecting the tube longitudinally through both layers, recovering roots from the sand layer only and isolating microorganisms from the recovered roots.

Agents, chemical or microbiological, which pass the two pests prescribed by this invention may then be further screened for inhibition of fungal infection in one or more than one additional test selected from:

(a) infection of sugar beet by *Aphanomyces cochlioides* at a temperature of from 12° to 15° C.;

(b) infection of peas by *Pythium ultimum* at a temperature of from 12° to 15° C.;

(c) infection of peas by *Pythium ultimum* at a temperature of from 24° to 27° C.;

(d) infection of peas by *Rhizoctonia solani* at a temperature of from 24° to 27° C.;

(e) infection of wheat by *Fusarium culmorum* at a temperature of from 18° to 21° C.;

(f) infection of soyabean by *Phytophthora megasperma* at a temperature of from 20° to 24° C.;

(g) infection of potato slice by *Fusarium moniliforme* at a temperature of from 20° to 24° C.;

(h) infection of a potato slice by *Fusarium sambusinum* at a temperature of from 20° to 24° C.; and, (i) infection of sugar beet by Phoma spp. at a temperature of from 15° to 19° C.

Thus, taking together all the possible components of the invention, potential BCAs may be isolated by a method which is designed only to recover root-active organisms, screened in two initial tests which identify organisms with high potential for activity and then they are screened in a series of rigorous tests which identify agents which subsequently prove to be highly robust when tested under a wide variety of field conditions. This represents a major advance over the traditional methods which, as previously stated, tend to reject organisms which pass the tests of this invention and pass very large numbers of organisms which the tests of the present invention show to be largely inactive or less active than control.

The invention then includes an antifungal agent exhibiting the same or better inhibition of fungal infection than a comparable chemical agent as indicated by the aforesaid screening tests of this invention.

By the method of this invention we have isolated and assessed four microorganisms which we find to be particularly active against a variety of fungal diseases, generally associated with damping-off, and, therefore, the invention also includes antifungal agents, comprising the microorganisms of the species *Pseudomonas fluorescens*, cultures of which were deposited on Sep. 1, 1989 under the terms of the Budapest Treaty with the National Collection of Industrial and Marine Bacteria Limited, 23 St. Marcer Road, Aberdeen AB2 1RY United Kingdom, under the Accession Numbers 40186, 40187, 40188 and 40190.

The invention also comprises an antifungal agricultural composition containing as active ingredient any one or more of the said microorganisms in admixture with a carrier composition acceptable in agricultural practice.

Examples of the types of agricultural formulations which may be employed are seed coatings compositions, liquid for root or soil drenching and granular or powder compositions. The base materials for these are well known in the art.

By way of example of the screening efficiency of the present invention, we used a traditional in vitro method to screen some 7000 isolates and found a "pass" rate of around 20% whereas with the method of the invention passed only some 4 to 5% of isolates. An important point, though, is that the collection of organisms which passed each of the two minimum tests of the invention were very similar whereas the traditional agar screen passed a quite dissimilar collection of organisms. Some of the organisms which might have been rejected had the traditional screening method been relied upon showed high activity in subsequent screening tests and in field trials. This is the principal advantage of the invention: the initial screen reduces the total number of organisms which require further screening and a high proportion of those which are indicated for further screening are subsequently found to display the sought-after activity in the field. We believe the reason to be as follows. The test parameters, for example temperature and nutrient composition, of the traditional method are optimised to promote growth of the microorganism in agar: such nurture is far removed from the harsh environmental reality of the conditions under which the intended use of the microorganism will be made. Consequently many of the microorganisms which survive this initial screen are generally weak, are only capable of survival in the closeted environment of the agar culture and subsequently fail as the more rigorous secondary and further screens begin to approximate more closely to the real field environment. On the other hand, within a batch of isolates there will be, and our experience indicates this to be true, strains of microorganisms which prefer the field conditions where, for example, temperatures are low or nutrients are less plentiful or of different composition. Such microorganisms do not culture well in the agar test and would normally be rejected. Our evidence is that the two screens at the heart of our invention provide test environments which are closer to field conditions and so give a more realistic indication of the ability of the microorganism to flourish in the environment in which it is to be used.

The present invention also provides a method of inhibiting fungal disease in a plant, comprising applying to the plant, the seed thereof or the growing medium for the plant an effective dose of an antifungal agent of the present invention.

Additionally, the invention provides a method of protecting crop plants from fungal infection comprising applying to the plants, the roots or seeds thereof or to soil surrounding the plants, a fungicidally effective dosage of one or more than one of the said *Pseudomonas fluorescens* strains.

Strain NCIB 40187 was isolated from wheat roots collected from plants grown in a field at a farm known as Badbury 2, Draycott Farm, Chiseldon, Swindon, Wiltshire, United Kingdom.

Strains NCIB 40186 and 40188 were isolated from soil taken from a field known as Stockoy Field in Jodoigne in Belgium.

Strain NCIN 40190 was isolated from the roots of wheat seedlings from Lower Garston field, Rushall Farm, Newbury, U.K.

There now follows a description of the isolation, characterisation and screening of the bacterial isolates for activity against several fungi which infect crop plants. Very large numbers of microorganisms were isolated, identified and screened in the manner hereinafter described, the four strains of the present invention being selected for their outstanding performance in the screening tests.

ISOLATION OF THE MICROORGANISMS

A tube was prepared from dialysis tubing 35 cm deep by 5.5 cm wide with a knot made 5 to 7 cm from one end. Fine sand was washed and dried and poured into the tube to a depth of 12 cm and moistened with 20 ml of distilled water. The tubes of sand were placed inside glass tubes (7 cm diameter by 30 cm deep) for support. The tubes were then closed at the bottom by a rubber bung covered in aluminium foil and at the top by a cotton wool plug and then wrapped in aluminium foil. The assembly was autoclaved twice at 121° C. for 60 minutes.

A soil sample was collected from the target soil site and maintained at 40% moisture at 4° C. until used, within two days of collection. The soil sample was sieved through a 4 mm sieve and added to the tubes to a depth of 3 cm on top of the sand A seed (pea, wheat, sugar beet, sunflower, maize or soybean) was sown and covered with soil to a total depth of 6 cm. The tubes were placed upright in a wire basket which was then enclosed in a plastics container with holes to allow for air exchange and to minimise evaporation losses. The baskets were then placed in a growth cabinet and incubated for four weeks at temperatures of 10° C. to 24° C and 70% relative humidity on a 16 hour day/8 hour night cycle.

After a four week incubation the plastic dialysis tubing was slit open with a pre-sterilised scalpel. The roots of each plant were teased away from the soil and sand, and the plant placed in a white plastic tray. The crown and tip regions of the plants were cut and washed separately in sterile water.

The cut sections were placed in sterile Erlenmeyer flasks containing 20 ml of deionised water and a layer of glass beads. The flasks were then shaken on an orbital incubator at 120 rpm for 30 minutes. Using a neat solution of the root and root and crown washings from the flasks, a 1:9 dilution was prepared in sterile Ringer's solution to a $10^{-3}$ dilution. An aliquot of 100 μl from each solution was then spread-plated on to the surface of three agar media having the following compositions:

1/10 TRYPTONE SOYA AGAR

Tryptone soya broth: 3.0 g
Bacteriological agar: 17.5 g
Deionised water: 1000 ml
[The medium was autoclaved at 121° C. for 15 minutes]

ROOT EXTRACT AGAR

Fresh wheat roots: 10 g
Agar No. 3: 17.5 g
Deionised water: 1000 ml
[The fresh roots were weighed and blended with a small amount of the deionised water using a food blender. The thick suspension was then placed inside a bag of four layers of small mesh muslin which was then suspended in the remaining deionised water in a 2 liter beaker and incubated at 20° C. for 4 days. The muslin bag was then removed and the agar added to the root extract. The medium was then autoclaved for 15 minutes at 121° C.]

SOIL EXTRACT AGAR

Soil sample: 10 g
Agar No. 3: 17.5 g
Deionised water: 1000 ml

[The soil was weighed and placed in the deionised water in a two liter beaker. The soil suspension was covered and incubated at 20° C. for four days after which it was drained through a quadruple layer of small mesh muslin. Agar was then added and the medium autoclaved at 121° C. for 15 minutes.]

There were three replicates for each dilution. The agar plates were incubated at 12° C. for up to five days after which the number of colonies on each plate was counted and recorded. Where possible a plate from each plant, niche and agar combination which contained fifty or fewer colonies was selected. When this was not possible, a grid of fifty intersects was drawn on the plate and colonies were taken which were on or nearest to each of the intersects. Thus colony selection was completely random.

The individual colonies were picked off the plates using a sterile loop and sub-cultured on 5 cm diameter petri dish plates containing 1/10 tryptone soya agar (1/10 TSA). The plates were then incubated at 12° C. for 5 days. The isolates were then checked for purity. Where there was a mixed culture, the isolate was streaked on to 1/10 TSA slope to obtain single colonies. One colony was chosen and subcultured on to 1/10 TSA. The culture collection was stored at 4° C.

CHARACTERISATION OF THE MICROORGANISM

Morphology

The morphological characteristics of the microorganism are as follows:

Cell Morphology: Gram-negative rods
Colony Morphology:
NCIB 40186: Off-white, round, regular, entire, low convex, smooth, shiny, semi-translucent, 1.5 to 2 mm diameter.
NCIB 40187: Off-white, round, regular, entire, raised, smooth, shiny, semi-translucent, 1 mm diameter.
NCIB 40188: Off-white, round, regular, entire, low convex, smooth, shiny, semi-translucent, 1.5 to 2 mm diameter.
NCIB 40190: Off-white, round, regular, entire, flat, smooth, shiny, semi-translucent, 1 mm diameter.

| Growth temperature: | All strains 37° C. +ve |
| --- | --- |
| | 41° C. −ve |
| | 45° C. −ve |
| Fluorescence | All strains +ve |
| Catalase | All strains +ve |
| Oxidase | All strains +ve |
| Fermentative in glucose OF | All strains −ve |

| RAPID TEST (API) | | | | |
| --- | --- | --- | --- | --- |
| | NCIB | | | |
| | 40186 | 40187 | 40188 | 40190 |
| Nitrate reduction | − | − | − | − |
| Indole production | − | − | − | − |
| Acid from glucose | − | − | − | − |
| Arginine dehydrolase | + | + | + | + |
| Urease | − | − | − | − |
| Aesculin hydrolysis | − | − | − | − |
| Gelatin hydroylsis | + | + | + | + |
| β-Galactosidase | − | − | − | − |
| Glucose assimilation | + | + | + | + |
| Arabinose assimilation | + | + | + | + |
| Mannose assimilation | + | + | + | + |
| Mannitol assimilation | + | + | + | + |
| N-acetylglucosamine assimilation | + | + | − | + |
| Maltose assimilation | − | − | − | + |
| Gluconate assimilation | + | + | + | + |
| Caprate assimilation | + | + | + | + |
| Adipate assimilation | − | − | − | + |
| Malate assimilation | + | + | + | + |
| Citrate assimilation | + | + | + | + |
| Phenylacetate assimilation | − | − | − | + |
| Cytochrome oxidase | + | − | + | + |

PRIMARY SCREENING

Soil Petri-dish Screen

Petri dishes (5 cm) were filled with 10 ml of potato dextrose agar (PDA). Agar plugs (5 mm) from a 7 day old culture of *Pythium ultimum* grown at 20° C. were placed centrally on to the PDA. The plates were incubated for 5 days at 20° C. during which the *P. ultimum* colonised the plate.

Minster Mendip Loam was autoclaved at 120° C. for 60 minutes. To this wheatgerm was added (1% w/w) and mixed well. Approximately 8 g of soil was placed into each Petri dish to cover the Pythium lawn.

The test bacteria were grown in 1/10 TSB or on 1/10 TSA plates for 48 hours at 12° C.

To each Petri dish, 2 ml of the culture was applied: duplicate plates were prepared.

Treatments

1/10 TSB alone
Metalaxyl (100 ppm)
Test Organism
1/10 TSB added to soil on PDA not inoculated with Pythium The plates were incubated for 4 days at 10° C.

Activity, scored on a scale of zero to 3, was selected on the basis of complete inhibition of fungal growth in the soil.

FUSARIUM POTATO SCREEN

A sterile filter paper disc (9 cm diameter) was thoroughly moistened with water and placed on the base of a sterile petri dish. Two plates were prepared for each treatment.

Fusarium cultures (*Fusarium sambusinum*, *Fusarium culmorum* and *Fusarium moniliforme*) were grown on potato dextrose agar for 14 days at 20° C. in the light in order to produce conidia. The conidia were then suspended in sterile saline (0.85%) and adjusted to a transmittance of 20% on a spectrophotometer at 420 nm.

One half loopful of bacteria grown on nutrient agar (Oxoid) for 24 hours at 20° C. was suspended in 2.5 ml of sterile saline. Captan at 2.0 g/l was prepared as a control. Saline alone was also used as a control.

Fusarium suspension (50 μl) was placed in a sterile microcentrifuge tube, one tube for each treatment.

One potato slice of less than 10 mm thickness, through which four wells had been cut using a 10 mm diameter cork borer, was placed in each petri dish. The surface of the potato slice was sterilised with ethanol and dried with sterile filter paper. The slices were used within 30 minutes of cutting (or 60 minutes if kept at 4° C.).

A 50 μl sample of the suspension of Fusarium spores ($10^6$ conidia/ml) was placed in three of the four wells in a potato slice. A sample of the bacterial suspension (50 μl, approximately $10^8$ cells per ml) was mixed with the Fusarium suspension in one of the three wells, and benomyl at 100 ppm in another, a third well serving as an uninoculated control.

The petri dishes were closed with their lids and incubated for 3 days at 20° C.

The level of diseased tissue was estimated on a subjective score of from 0 to 3.

SCREENING AGAINST PHOMA BETAE

Pieces of sugar beet, 2.5×2.5×1.5 mm, were excised from the interior of the root and moistened with about 13 ml of sterile water in a plastics container.

A sample of a culture of Phoma betae, with or without a sample of the putative antifungal microorganism, was poured on to the surface and the pieces incubated for 3 weeks.

At the end of the incubation period, the beet samples were assessed for rot.

SUGAR BEET/SOIL SCREEN

Natural soil which was known to cause "damping-off" of sugar beet was brought to a humidity of 45%. Naked sugar beet seed and seed coated with test bacteria were sown in the soil. The samples were then incubated for 10 days with a 12 hour day illumination at 15° C. The antifungal efficacy of the bacteria was assessed on the basis of the number of seedlings which emerged compared with chemical control by Tachigaren/TMTD.

SECONDARY SCREENING

To test the effectiveness of the selected microorganism two screens were used: Pythium ultimum and Rhizoctonia solani.

Cultures of P. ultimum and R. solani were raised on PDA plates for 7 days at 20° C.

A mixture of 200 g of silver sand, 5 g cornmeal, 4 g Beemax wheatgerm and 40 ml water was autoclaved at 120° C. for 20 minutes then placed in a flask and inoculated with ¼ of a plate of Pythium. The same substrate, but without the cornmeal was used for Rhizoctonia.

The flasks were incubated at 20° C. for 7 days.

Dilution Series

The contents of each Pythium ultimum flask were mixed with fine sand to a final weight of 300 g.

One flask of Pythium in 8 liters of Mendip Minster Loam = 2 Normal (2N)

This is diluted with clean Mendip loam to further dilutions which are required. Isolates were normally screened against Pythium at N/8 and N/32 at 12°–15° C.

¾ flask of Rhizoctonia solani inoculum in 6 liters of Mendip Minster Loam = Normal. Concentration at N/4 and N/16 were used in the screen.

The trial was carried out in three inch pots, the pots filled to ¾ with infected soil. Five peas were sown in each pot and covered with clean soil. 35 ml of water or bacterial suspension were added as a drench to each pot. Five replicate pots were prepared for each treatment. In the BCA screens, the bacteria were grown for 48 hours at 20° C. in 1/10 TSB. The whole suspension (35 ml) was added to the pots Controls were normally 1/10 TSB and chemical. Pencycuron was added as a drench at 10, 100 or 200 ppm concentrations to the Rhizoctonia screens and metalaxyl as a drench to the Pythium screens at 100 ppm.

Plants were grown to test for R. solani for 7 to 14 days at 202 –25° C. and for Pythium at 12° to 15° C. for 14 days. Seedling emergence was monitored weekly. The plants were watered daily. Particular care was taken to ensure that the soil was kept moist during the tests as both diseases incite damping-off.

SCREENING AGAINST PHYTOPHTHORA MEGASPERMA

A 5 mm diameter plug taken from a plate culture of P. megasperma was cultured on a 9 cm diameter plate on V-8 medium for 13 days at 25° C. V-8 medium as the following composition:

| V-8 Campbell juice | 180 ml |
|---|---|
| CaCO$_3$ | 2.7 g |
| Distilled water | 720 ml |
| Difco agar | 13.5 g |

[The components, other than the agar, were mixed and heated to steam heat for 30 minutes, filtered, pH adjusted to 7.2, the agar added and the medium sterilized at 120° C. for 20 minutes.]

Moist millet (50 g plus 20 ml of distilled water) was sterilised twice at 110° C. for 45 minutes. A ¼ P. megasperma plate was placed upside down on the surface of the millet and incubated in the dark for 28 days at 25° C.

The P. megasperma infected millet (weighing 22.5 g) was thoroughly mixed with sterilised soil (1477.5 g) and water (112.5 g) in a mixer. The soil used was a 1:1:1 v/v mixture of silver sand, field soil at pH7 and moss peat which had been sterilised at 100° C. for one hour.

An amount of 500 g of the infected millet/soil mixture was weighed into Leonard jars which were then covered with plastics closure plates until required. The bottom water reservoir of the Leonard jars was filled with 100 ml of distilled water.

Four planting holes were made in the surface of the millet/soil mixture and into each a soybean (c.v. Azzurra) was sown and covered with the surrounding mixture.

Cultures of the test organism were prepared on nutrient agar plates cultured at 28° C. for 24 hours and in 250 ml NB flasks (150 ml NB) cultured for 24 hours at 28° C. A sample of 75 ml of the culture was centrifuged at 8000 rpm for 5 minutes at 20° C. The supernatant was discarded, a further 75 ml sample added, recentrifuged and the supernatant again discarded. The pellet remaining in the centrifuge tubes was repeatedly washed with 5 ml amounts of saline solution (9.2 g/l). Finally the pellet was dispersed into suspension in 150 ml of saline.

An injection of 30 ml of the saline suspension was made into each of the Leonard jars from a 60 ml syringe.

For comparison with chemical agents, 30 ml samples of a solution of 285.5 g of metalaxyl 35% (Trade Mark APRON) in 500 ml of distilled water were injected into the Leonard jars acting as control.

Uninfected controls were also established using samples of uninfected millet/soil mixture.

The seeds were then induced to grow in a growth cabinet at 20°±2° C. under illumination of 15-17,000 lux. was based on percent emergence compared with chemical control.

FUSARIUM CULMORUM SCREEN

A culture of *Fusarium culmorum* was grown in PDA for 10 days at 20° C. to permit conidia to form. The conidia were collected and counted to a range of concentrations of from $10_4$ to $10_8$ conidia per ml. From this stock, 5 ml were added to 100 g of wheat seed in a bottle which was then rotated overnight at 10° C.

A sample of the infected seed was soaked in a mixture of the test bacteria and silver sand for 60 minutes prior to sowing to apply a coat of about $10^6$ cells per seed. A second sample was treated with benomyl (100 ppm) as a chemical control.

One hundred seeds were sown in a peat based compost in a seedling tray at a depth of 2 cm. The compost was watered at the start of the trial, placed at 20° C. for 2 weeks and watered again on the fifth day after sowing. After this initial watering of the compost to encourage germination of the seeds the compost was allowed to dry to encourage the disease to develop.

The seedlings were monitored for establishment and disease development. Disease symptoms were scored on a scale of from zero (no symptoms) to 4 (severely diseased).

RESULTS

Some 7000 soil bacterial isolates were screened by the tests described above. Table 1 below summarises the results of these tests. The figures in the columns are on a scale of from zero (no antifungal effect) to 3 (no discernible disease symptoms). Also included in the Table is a comparative example of a typical ineffective bacterial strain, designated 53/87.

TABLE 1

|  | 40186 | 40187 | 40188 | 40190 | 53/87 |
|---|---|---|---|---|---|
| PRIMARY SCREENS NCIB | | | | | |
| *Fusarium culmorum* | 1 | 2 | 0 | 2 | 1 |
| *Fusarium moniliforme* | 1 | 1 | 0 | 1 | 1 |
| *Fusarium sambusinum* | 0 | 1 | 0 | 0 | 1 |
| *Pythium ultimum* | 2 | 3 | 2 | 2 | 0 |
| Aphanomyces | 3 | 1 | 0 | 2 | 0 |
| *Phoma betae* | 2 | 0 | 3 | 1 | 0 |
| Sugar beet/soil | 3 | 2 | 2 | 3 | 0 |
| SECONDARY SCREENS NCIB | | | | | |
| *Rhizoctonia solani* | 0 | 3 | 3 | 0 | 0 |
| *Pythium ultimum* 15° C. | 3 | 3 | 3 | 0 | 0 |
| *Pythium ultimum* 24° C. | 3 | 2 | 2 | 2 | 0 |
| *Fusarium culmorum* | 2 | 2 | 2 | 2 | 0 |
| *P. megasperma* | 2 | 1 | 1 | 1 | 0 |

FIELD TRIALS DATA 1989

The strains which showed most promise in the primary and secondary screening were selected for field trials as biological control agents against "damping-off" disease in peas and sugar beet.

BRIEF DESCRIPTION OF THE DRAWINGS

FIG. 1 illustrates the results obtained with strain NCIB 40186 against damping off in peas. This trial was conducted in U.K. Control obtained with this strain was around 80% of the control given by a chemical treatment with metalaxyl (APRON, Trade Mark). Strain NCIB 40187 was largely ineffective in this trial.

FIGS. 2 and 3 show the results of field trials on sugar beet using strains NCIB 40186 and 40190. These trials were conducted in Belgium. Six field sites were selected. Three sites (1,3 and 6) were sown with sugar beet in March and the remaining three sites were sown in May. FIG. 2 shows the results at the first count which was made 3 weeks after sowing and FIG. 3 shows the results after 6 to 8 weeks after sowing.

In summary, these results show that damping-off in peas, caused by *Pythium ultimum* is reduced by application of strain NCIB 40186 at a level comparable with that obtained with chemical treatment with metalaxyl. The sugar beet results show improved seedling establishment with application of strains NCIB 40186 AND 40190 compared with untreated controls at all six sites. At three sites seedling establishment in the presence of the strains was comparable to that obtained with metalaxyl.

FIELD TRIAL DATA FOR 1990

During 1990 field trials of microorganisms NCIB 40186 and 40190 have been conducted on its potential for inhibiting Pythium spp. The trials were conducted in The United States of America, Belgium and France and the results will be reported below. For the purpose of the trials the microorganism was applied as a seed soak followed by drying in sand for the European studies and as a gum/peat formulation for USA. Further trials continue in other parts of the world where "damping-off" diseases are endemic, for example, in vegetable crops in Malaysia. Although we are unable to present the results from the trials around the world, simply because the trials are not yet complete and, as will be appreciated, cannot be accelerated because of the seasonal strictures on agricultural procedures, initial indications from our testers are favourable and thus, these particular microorganisms, at least, shows great potential for a commercial biological control agent. Further testing of the other microorganisms mentioned herein continues in the laboratory and growth room in accordance with normal practice for efficacy and safety both to man and the environment. Results currently to hand confirm the potential found earlier and as reported herein.

The strains NCIB 40186 and 40190 were tested against damping-off in sugar beet in trials in nine plots in Belgium and France. During sowing in early spring the weather was very warm and dry which caused some problem for disease development of damping-off in sugar beet. In each of the test plots a total of 200 seeds were sown. To date results from nine of the trials are available.

BELGIAN AND FRENCH TRIALS 1990

Test crop: Sugar Beet
Chemical control: tachigaren/TMTD

| Trail No. | Number of seeds out of 200 which emerged | | | |
|---|---|---|---|---|
| | Untreated Control | Chemical Treatment | NCIB 40186 | NCIB 40190 |
| 1 | 93 | 125 | 130* | 114 |
| 2 | 118 | 141* | 124 | 127 |
| 3 | 118 | 157* | 146* | 138* |
| 4 | 107 | 139* | 131* | 122* |
| 5 | 120 | 150* | 128 | 130 |
| 6 | 84 | 116* | 111* | 114* |
| 7 | 135 | 153* | 143 | 138 |
| 8 | 119 | 148* | 141 | 135 |
| 9 | 134 | 155* | 144 | 144 |

*LSD at 5% probability

FRENCH TRIALS 1990

Test Crop: Peas
Chemical Controls: as shown below
No. of plants refers to the mean number of plants which emerged on a strip 5 meters long 22 days after treatment.

Column 2 in the Tables gives number of plants which emerged from 200 seeds 22 days after sowing. The letters appearing after the numbers indicate statistical significance. There is no significant difference at the 5% probability level between entries with a letter in common.

CONTROL TREATMENTS

Tests conducted in normal field soil, without any added pathogen.

| Treatment | Number emerged |
|---|---|
| Untreated seed | 172.58 AC |
| NCIB 40186 - 107 cells per seed | 184.75 A |
| APRON - 30 g a.i./100 Kg of seed | 171.50 AC |
| RIDOMIL 2E metalaxyl furrow drench | 181.00 A |
| Blank seed 100 cell/seed | 176.00 AC |

TEST TREATMENTS

Pathogen (Pythium) was added at a rate of 200 g/meter row.

| Treatment | Number emerged |
|---|---|
| Untreated seed | 111.25 I |
| NCIB 40186 - 107 cells per seed | 144.75 DG |
| APRON - 30 g a.i./100 Kg of seed | 157.25 BCDF |
| RIDOMIL 2E metalaxyl furrow drench | 164.25 AD |
| Blank seed 100 cell/seed | 119.88 HI |

CALIFORNIAN (USA) TRIALS 1990

Test Crop: peas
Test Pathogen: Pythium at 30 g/meter row.

| Treatment | % emerged |
|---|---|
| No added pathogen, no treatment | 93.13 AB |
| Pathogen + NCIB 40186 — 107 cells/seed | 75.31 BCD |
| Pathogen + Blank seed — 100 cells/seed | 51.56 EF |
| Pathogen + APRON-30 g a.i./100 Kg | 92.81 AB |

MISSISSIPPI (USA) TRIAL 1990

Test Crop: maize
Test Pathogen: Fusarium
(i) at 10 g/meter row
(ii) at 30 g/meter row
Emergence is quoted at % after 15 days after sowing.

| Treatment | % emerged |
|---|---|
| No added pathogen, no treatment | 65.833 C |
| No added pathogen, NCIB 40186 107 cells/seed | 67.917 C |
| No added pathogen CAPTAN as seed treatment | 69.583 BC |
| Pathogen (i), no treatment | 51.250 D |
| Pathogen (i) + NCIB 40186 107 cell/seed | 80.000 AB |
| Pathogen (ii), no treatment | 69.375 BC |
| Pathogen (ii) + NCIB 40186 107 cells/seed | 82.708 A |
| Pathogen (ii) + CAPTAN as seed treatment | 63.958 C |

What is claimed is:

1. In a method for the screening of a putative antifungal agent, the improvement which comprises assessing the inhibitory effect of said agent on fungal infestation in two tests, wherein the first test comprises preparing a mycelium of a pathogen of the Pythium spp in a layer of culture medium, placing a layer of sterile soil on the culture layer, adding an aliquot of a putative antifungal agent to the soil layer, incubating the test unit and assessing the inhibitory effect of the antifungal agent on growth of the pathogen; and, the second test comprises inoculating a soil sample with a pathogenic fungus sowing in the fungus-infested soil a seed of a plant susceptible to infection by the fungus, applying an aliquot of a putative antifungal agent to the soil, allowing the seed to germinate and a plant to grow therefrom and assessing the inhibitory effect of the said antifungal agent on plant health compared with an uninfected control.

2. A method as claimed in claim 1, in which the plant susceptible to infection by fungus is sugar beet.

3. A method as claimed in claim 1 or claim 2, in which the putative antifungal agent is a microorganism.

4. A method as claimed in claim 3, in which the said microorganism is a root-colonising microorganism.

5. A method as claimed in claim 4, in which the said root-colonising microorganism is isolated from a soil sample by a method which comprises placing within a sealable container a layer of moist sterile sand, placing a layer of the soil sample in moist condition thereupon and sowing in the soil sample a seed of a plant susceptible to infection by the fungus sealing the container, placing the container under environmental conditions conducive to disease development, allowing the seed to germinate and the roots thereof to extend from the soil layer into the sand layer, dissecting the container longitudinally through both layers, recovering roots from the sand layer only and isolating microorganisms from the recovered roots.

6. A method as claimed in claim 1 in which an agent which exhibits disease inhibition in both of said tests is further screened for inhibition of fungal infection by repeating said two tests at least one additional test selected from the group consisting of:

(a) infection of sugar beet by *Aphanomyces cochlioides* at a temperature of from 12° to 15° C.;

(b) infection of peas by *Pythium ultimum* at a temperature of from 12° to 15° C.;

(c) infection of peas by *Pythium ultimum* at a temperature of from 24° to 27° C.;

(d) infection of peas by *Rhizoctonia solani* at a temperature of from 24° to 27° C.;

(e) infection of wheat by *Fusarium culmorum* at a temperature of from 18° to 21° C.;

(f) infection of soybean by *Phytophthora megasperma* at a temperature of from 20° to 24° C.;

(g) infection of potato slice by *Fusarium moniliforme* at a temperature of from 20° to 24° C.;

(h) infection of a potato slice by *Fusarium sambusinum* at a temperature of from 20° to 24° C.; and, (i) infection of sugar beet by Phoma spp. at a temperature of from 15° to 19° C.

7. An antifungal agent comprising *Pseudomonas fluorescens* deposited with the National Collection of Industrial and Marine Bacteria Limited under the Accession Number 40186.

8. An antifungal agent comprising *Pseudomonas fluorescens* deposited with the National Collection of Industrial and Marine Bacteria Limited under the Accession Number 40187.

9. An antifungal agent comprising *Pseudomonas fluorescens* deposited with the National Collection of Industrial and Marine Bacteria Limited under the Accession Number 40188.

10. An antifungal agent comprising *Pseudomonas fluorescens* deposited with the National Collection of Industrial and Marine Bacteria Limited under the Accession Number 40190.

11. An antifungal agricultural composition comprising as active ingredient an antifungal agent claimed in any one of claims 7-10, in admixture with a carrier composition acceptable in agricultural practice.

12. A method of inhibiting fungal attach on a plant, comprising applying an effective dose of an antifungal agent as claimed in any one of claims 7-10, to the locus of the plant.

* * * * *